United States Patent [19]

Petöcz et al.

[11] Patent Number: 4,883,798

[45] Date of Patent: Nov. 28, 1989

[54] PHARMACEUTICAL COMPOSITIONS

[75] Inventors: Lujza Petöcz; István Simonyi; Iván Beck; Gábor Gigler; Márton Fekete; Enikö Szirt née Kiszelly; Attila Mándi; Frigyes Görgényi; András Dietz; Elemér Jákfalvi; Katalin Zukovics née Sümeg; Klára Gadó; Mária Hegedüs, all of Budapest, Hungary

[73] Assignee: EGIS Gyogyszergyar, Budapest, Hungary

[21] Appl. No.: 221,529

[22] Filed: Jul. 20, 1988

[30] Foreign Application Priority Data

Jul. 22, 1987 [HU] Hungary .............................. 3375/87

[51] Int. Cl.$^4$ ........................................... A61K 31/505
[52] U.S. Cl. ..................................... 514/256; 514/275
[58] Field of Search ............................. 514/256, 275

[56] References Cited

U.S. PATENT DOCUMENTS

| | | | |
|---|---|---|---|
| 3,993,761 | 11/1976 | Grunberg et al. | 514/275 |
| 4,053,608 | 10/1977 | Morisawa et al. | 514/352 |
| 4,087,528 | 5/1978 | Perum et al. | 514/275 |
| 4,332,796 | 6/1982 | Los | 514/157 |
| 4,461,765 | 7/1984 | Takagishi et al. | 514/158 |

OTHER PUBLICATIONS

Francalanci et al., Chem. Abst. 79(25):142830a(1973).

Primary Examiner—Stanley J. Friedman
Attorney, Agent, or Firm—Keil & Weinkauf

[57] ABSTRACT

The compounds of the general Formula I

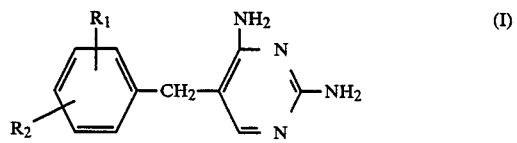

(wherein $R^1$ and $R^2$ may be the same or different and each stands for hydrogen, hydroxy, $C_{1-6}$ alkoxy, $C_{1-6}$ alkoxy-$C_{1-6}$ alkoxy, $C_{2-6}$ alkenyloxy or phenyl-($C_{1-3}$ alkoxy), or $R^1$ and $R^2$ together form $C_{1-2}$ alkylenedioxy; with the proviso that at least one of symbols $R^1$ and $R^2$ is other than hydrogen and with the further proviso that $R^1$ and $R^2$ can not represent 3,4-dimethoxy substitution) and their pharmaceutically acceptable acid addition salts exhibit useful analgesic, antipyretic, anti-inflammatory, anti-anginal and antioxidant effect.

9 Claims, No Drawings

PHARMACEUTICAL COMPOSITIONS

The invention relates to pharmaceutical compositions comprising as active ingredient 2,4-diamino-5-(substituted benzyl)-pyrimidine derivatives.

According to an aspect of the present invention there are provided pharmaceutical compositions comprising as active ingredient an effective amount of at least one compound of the general Formula I

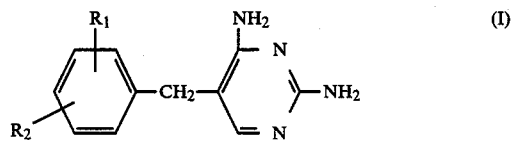

(wherein $R^1$ and $R^2$ may be the same or different and each stands for hydrogen, hydroxy, $C_{1-6}$ alkoxy, $C_{1-6}$ alkoxy-$C_{1-6}$ alkoxy, $C_{2-6}$ alkenyloxy or phenyl-($C_{1-3}$ alkoxy), or $R^1$ and $R^2$ together form $C_{1-2}$ alkylenedioxy; with the proviso that at least one of symbols $R^1$ and $R^2$ is other than hydrogen and with the further proviso that $R^1$ and $R^2$ can not represent 3,4-dimethoxy substitution) or a pharmaceutically acceptable acid addition salt thereof in admixture with suitable inert solid or liquid pharmaceutical carriers and/or auxiliary agents.

The pharmaceutical compositions according to the present invention exhibit particularly useful analgesic, antipyretic, anti-inflammatory, anti-anginal and/or antioxidant effect.

It has been found that the compounds of the general Formula I and pharmaceutically acceptable acid addition salts thereof possess useful and characteristic features in human clinical use. The analgesic and anti-inflammatory therapeutical indexes of the compounds of the general Formula I surpass those of the reference compound Indomethacin by one and two order(s) of magnitude, respectively. These activities are accompanied by an antipyretic effect being in the order of magnitude of that of acetyl salicylic acid and an antioxidant effect being identical with or by two orders of magnitude higher than that of the reference compounds. The compounds of the general Formula I do not induce gastric mucosal damage even in toxic doses. The majority of the compounds of the general Formula I exert an antianginal effect on rats stronger than that of prenylamine.

The following compounds of the general Formula I show particularly valuable pharmaceutical effects:
2,4-diamino-5-(4-methoxy-benzyl)-pyrimidine;
2,4-diamino-5-(3-methoxy-benzyl)-pyrimidine;
2,4-diamino-5-(3,5-dimethoxy-benzyl)-pyrimidine;
2,4-diamino-5-(2,4-dimethoxy-benzyl)-pyrimidine;
2,4-diamino-5-(2,3-dimethoxy-benzyl)-pyrimidine;
2,4-diamino-5-(3,4-methylenedioxy-benzyl)-pyrimidine;
2,4-diamino-5-(3-methoxy-4-ethoxy-benzyl)-pyrimidine;
2,4-diamino-5-(3-methoxy-4-allyloxy-benzyl)-pyrimidine;
2,4-diamino-5-(3-methoxy-4-n-butoxy-benzyl)-pyrimidine;
2,4-diamino-5-(3-methoxy-4-methoxyethoxy-benzyl)-pyrimidine;
2,4-diamino-5-(3-methoxy-4-benzyloxy-benzyl)-pyrimidine;
2,4-diamino-5-(3-methoxy-4-hydroxy-benzyl)-pyrimidine
or a pharmaceutically acceptable acid addition salt thereof.

The salts of the compounds of the general Formula I may be pharmaceutically acceptable acid addition salts formed with inorganic or organic acids (e.g. hydrochlorides, hydrobromides, sulfates, acetates, citrates, maleates, fumarates, tartarates, lactates, ascorbinates etc.).

The pharmaceutical activity of the compounds of the general Formula I is proved by the following tests.

(1) Acute toxicity in mice

Method

The experiments were performed in CFLP white mice of both sexes of 18–22 g body weight in groups of at least 10 animals. The test compound was applied p.o. dissolved in a solution containing 0.2% Tween-80 in distilled water in a volume of 20–30 ml/kg. The observation period after treatment lasted for 14 days. Statistical evaluation was carried out as described by Litchfield-Wilcoxon's method. The results are summarized in Table I.

TABLE I

| Acute toxicity on mice | | |
|---|---|---|
| Test compound No. of example | | $LD_{50}$ mg/kg |
| 1 | about | 350 |
| 2 | about | 410 |
| 3 | about | 800 |
| 4 | about | 2000 |
| 5 | about | 500 |
| 6 | about | 750 |
| 7 | about | 350 |
| 8 | about | 1500 |
| 9 | | >2000 |
| 10 | | <500 |
| 11 | | >2000 |
| 12 | | >2000 |
| Indomethacin | | 22.5 |
| Acetilsalicylic acid | | 1350 |

(2) Analgesic activity "Writhing test" in rats

Method

Rats weighing 130–170 g were administered intraperitoneally 0.75% (v/v) acetic acid in a volume of 8 ml/kg. Five minutes after treatment with acetic acid the total number of characteristic writhing reactions was counted for 10 minutes and expressed as percentage of the control group. One hour prior to the injection of acetic acid the rats were treated in groups of 10 animals either with the test compound or with the vehicle (control) p.o. The results are disclosed in Table II.

TABLE II

| Analgesic effect on rats | |
|---|---|
| Test compound No. of Example | Therapeutical Index |
| 1 | about 8.1 |
| 2 | about 5.9 |
| 3 | about 8.0 |
| 4 | about 33.3 |
| 5 | about 5.0 |
| 6 | about 57.7 |
| 7 | about 7.6 |
| 8 | about 42.9 |
| 9 | >125.0 |
| 10 | <14.3 |
| 11 | >37.0 |
| 12 | >40.0 |

TABLE II-continued

| Analgesic effect on rats | |
|---|---|
| Test compound No. of Example | Therapeutical Index |
| Indomethacin | 4.8 |

(3) Antipyretic effect in rats

Method

The experiments were performed in groups of 10 Wistar rats of both sexes weighing 160-200 g. Fever was induced by 20% brewer yeast suspended in 0.9% saline solution, applied subcutaneously in a volume of 2 ml/rat distributed at various sites of the back. After 18 hours the test compound or the vehicle (control) was administered in volume of 10 ml./kg p.o. During this period the rats were fasted but received drinking water ad libitum. The rectal temperature of the animals was measured with a Thermotest thermometer 2 days before the administration of the test compound and after treatment every 60th minute. Animals with an increase of body temperature less than 0.8° C. were excluded from the experiment. The results were evaluated according to the statistical method of Duncan and are set forth in Table III.

TABLE III

| Antipyretic effect in rats | | |
|---|---|---|
| Test compound No. of Example | Dose mg/kg | Maximal temperature decrease, °C. |
| 1 | 200 | 0.9 |
| 6 | 100 | 1.0 |
| 7 | 100 | 0.7 |
| 8 | 100 | 0.8 |
| Acetylsalicylic acid | 200 | 1.0 |

(4) Effect of chemiluminescence

Method

The test-compounds were dissolved in dimethyl-sulfoxide (DMSO) in a concentration of $10^{-1}$M, dilutions were made in the incubation medium employed. Heparinized blood (10 IU/ml) was taken from healthy volunteers. The blood was diluted with equal wolume of dextran, then the white blood cells were separated by sedimentation. The granulocytes were separated by Uromio gradient. The mononuclear cells were separated by centrifugation in Ficoll-Uromio gradient (specific gravity 1,078; 30 min., 2000 rpm). The cells were washed twice with Parker IC-199 medium and suspended in the same medium ($10^6$ cells/ml). The cell suspension was put in dark box for 15 min. Luminol was dissolved in concentrated NH$_4$OH and diluted in the following solution:

50 ml Tris-Parker medium (containing 1,2 g Tris, pH=7,4)
150 ml Parker tissue culture medium
4 ml glucose 40% w/v in water The final concentration of Luminol was 32 μM. The Luminol solution (500 μl) was measured in plastic vials and put in dark (37° C.). The reaction was started by addition of the cells and stimulating agent (Phytohaemaglutinin-PHA-10 μg/ml).

The vials were continuously and gently shaken and the PHA stimulation was measured in every 2,5 min. for 15 min. in a Beckmann LS-100 spectrometer (coincidence switched off). The percentage of the counts measured was calculated in comparison with the solvent treated control cells. At least 5 concentrations of each compound were investigated in at least 3 parallels.

The results are summarized in Table IV.

TABLE IV

| Measurement of chemiluminescence of granulocytes | |
|---|---|
| Test compound No. of Example | IC$_{50}$ M |
| 1 | about $10^{-4}$ |
| 2 | about $10^{-4}$ |
| 7 | about $10^{-6}$ |
| 8 | about $10^{-6}$ |
| 9 | about $10^{-6}$ |
| Indomethacin | $10^{-4}$ |
| Phenylbutazone | $10^{-4}$ |
| Piroxicam | $10^{-4}$ |

On the basis of the chemiluminescence measurements compounds of the general Formula I inhibit the formation of free oxygen radicals. These free radicals cause tissue damages, the inhibition of the formation of these radicals may give a therapeutic usefulness. Agents active in this respect may be employed as anti-inflammatory agents and may inhibit the process of ageing. As it is known, in the process of ageing the damage of structural elements caused by free oxygen radicals plays an important role.

The following reference compounds are used in the above tests:

Phenylbutazone=3,5-dioxo-1,2-diphenyl-4-(n-butyl)-pyrazolidine;

Indomethacine=1-(p-chloro-benzoyl)-5-methoxy-2-methyl-1H-indole-3-acetic acid;

Piroxicam=4-hydroxy-2-methyl-N-2-pyridyl-2H-1,2-benzothiazine-3-carboxamide-1,1-dioxide.

The above tests are carried out by standard methods. Reference is made to the following citations: Litchfield, J. T., Wilcoxon, F.: J. Pharmacol. Exp. Ther., 96, 99-113 (1949); Newbould, B. B.: Brit. J. Pharmacol. 35, 487 (1969); Shay, H., Kemarov, S. A., Fels, S. S., Meranze, D., Gruenstein, M., Siplet, H.: Gastroenterology 5, 45 (1945); Stickney, J. C., Northup, D. W., Van Liere, E. J.: Arch. int. Pharmacodyn. 147, 113 (1964); Winter, C. A., Risley E. A., Nuss, G. W.: Proc. Soc. Exp. Biol. Med. 111, 544-547 (1962).

The pharmaceutical compositions of the present invention may be prepared by methods known per se by admixing a compound of the general Formula I or a pharmaceutically acceptable acid addition salt thereof with suitable inert solid or liquid pharmaceutical carriers.

The compounds of the general Formula I or pharmaceutically acceptable acid addition salts thereof may be finished in forms suitable for oral, rectal or parenteral administration. The compositions suitable for oral administration may be e.g. tablets, pills, coated pills, dragées, enterosolvent tablets or dragées or capsules. The active ingredient content of the said compositions may be preferably between about 100 mg and about 500 mg.

The oral compositions may contain carriers and/or auxiliary agents generally used in pharmaceutical industry, e.g. lactose, starch, magnesium stearate, sodium citrate, calcium carbonate, dicalcium phosphate, starch derivatives (e.g. carboxymethyl starch), silicic acid or binding agents (e.g. polyvinyl pyrrolidone etc.) or sliding agents (e.g. magnesium stearate or talc etc.).

The compositions suitable for oral administration may also be finished in the form of aqueous suspensions or dispersions. The said compositions may comprise as diluent e.g. water, ethanol, propylene glycol or glycerol in addition to usual additives, e.g. colour-improving agents, dyestuffs, emulsifying or stabilizing agents (e.g. methyl-p-hydroxy benzoate etc.).

The tablets may be prepared according to a dry or wet granulating procedure. Dragées are obtained by preparing the dragée core and coating the same with a suitable coating layer by known methods. Capsules are prepared by filling a suitable mixture of the components into soft or hard gelatine capsules.

Suppositories suitable for rectal administration contain generally from about 0.01 g to about 0.5 g of the active ingredient. Suppositories may be prepared by uniformly distributing the active ingredient in the melt suppository base (e.g. cocoa butter, Witepsol H15 etc.), filling the melt into suitable forms, cooling the same and packing the suppositories into aluminum foil or tinfoil.

Injections suitable for parenteral use may be administered intravenously, intramuscularly, intraperitoneally or subcutaneously. The active ingredient content of the injectable solutions may vary preferably between about 0.005 g/ml and about 0.25 g/ml. Injectable solutions are advantageously filled into 1 ml or 2 ml ampoules; the active ingredient content of the said ampoules amounts preferably to about 0.0025–0.25 g/ampoule. Injectable solutions suitable for parenteral administration contain as diluent preferably water, sesam oil, peanut oil, aqueous propylene glycol or any other pharmaceutically acceptable solvent. It is preferred to prepare aqueous solutions. Injectable solutions comprise the compound of the general Formula I preferably in the form of a water soluble salt thereof. Aqueous solutions may be buffered, if necessary, by methods known per se or can be made isotonic with the aid of a suitable amount of sodium chloride or glucose. The solutions thus obtained may be sterilized by known methods, if necessary.

The daily dosage of the compound of the general Formula I or an acid addition salt thereof may vary between wide ranges. Adult patients may receive for the relief of mild or medium-strong pains (e.g. headache, tooth-ache, lumbago, back-ache, neuralgia, myalgia, cold accompanied by fever, post-operation pains etc.) one or two tablets having an active ingredient content of 10–500 mg twice or three times a day.

In case of chronical rheumatic inflammations and degenerative rheumatism 8–10 tablets per day may be administered, particularly two tablets every 6th–8th hour.

The preferred daily dose for children is 3–4 times half a tablet or one tablet having an active ingredient content of 10–250 mg.

The daily dosage of the compounds of the general Formula I amounts generally to about 5–4000 mg in various indications.

As analgesic and antipyretic agent the daily dose amounts to 5–2000 mg, administered in three or four portions a day. Children up to an age of 11 years may preferably receive a daily dose of 5–250 mg, while adults may preferably obtain 50–2000 mg.

In the treatment of rheumatic inflammations and rheumatism of various origin (degenerative or nonarthritic) the preferred dose may be about 100–1500 mg for children and 300–4000 mg for adults.

We wish to emphasize that the above ranges are but of an information character and the actual dose is always determined by taking into consideration all circumstances of the given case and the prescriptions of the physician. Thus the actual dose may be lower or higher than the above range as well.

The compounds of the general Formula I and pharmaceutically acceptable acid addition salts thereof may be prepared by methods disclosed in the prior art.

Thus the compounds of the general Formula I and pharmaceutically acceptable acid addition salts may be prepared e.g. by (a) reacting a compound of the general Formula VIII

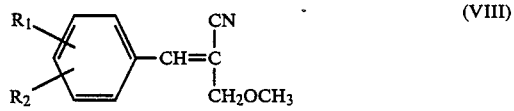

with a diethylene glycol mono lower alkyl ether of the general Formula IV

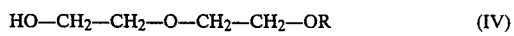

and reacting the compound of the general Formula V

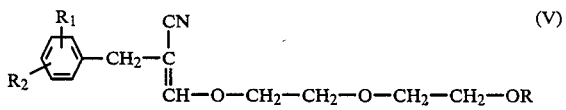

thus obtained with guanidine or an acid addition salt thereof; or (b) reacting a compound of the general Formula VIII with an ethylene glycol mono lower alkyl ether of the general Formula VI

and reacting the compound of the general Formula VII

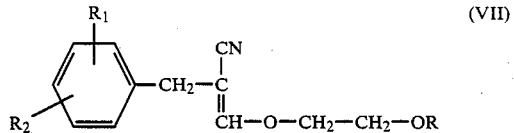

thus obtained with guanidine or an acid addition salt thereof;

and, if desired, converting a group $R^1$ and/or $R^2$ into another group $R^1$ and/or $R^2$, respectively, and if desired, converting a compound of the general Formula I into a pharmaceutically acceptable acid addition salt thereof (in the general Formulae R stands for lower alkyl and $R^1$ and $R^2$ are as stated above).

According to a further aspect of the present invention there is provided the use of a compound of the general Formula I or a pharmaceutically acceptable acid addition salt thereof for the preparation of pharmaceutical compositions having analgesic, antipyretic, anti-inflammatory, anti-anginal and/or antioxidant effect.

According to a still further aspect of the present invention there is provided the use of the compounds of the general Formula I and pharmaceutically acceptable acid addition salts thereof for analgesic, antipyretic, anti-inflammatory, anti-anginal and/or antioxidant treatment.

The advantage of the pharmaceutical compositions of the present invention resides in the fact that the analgesic and anti-inflammatory effect of the compounds of the general Formula I signficantly surpass that of the commercially available products generally used in this field of activity and simultaneously the compounds of the general Formula I are void of the gastric mucosa damaging effect characteristic of known anti-inflammatory and analgesic agents. Thus the compounds of the general Formula I exhibit the desired analgesic and anti-inflammatory effect without inducing undesired ulcerous side-effects.

Further details of the present invention are to be found in the following Examples without limiting the scope of protection to the said Examples.

EXAMPLES

I. Preparation of compounds of the general Formula I

EXAMPLE 1

2,4-Diamino-5-(4-methoxy-benzyl)-pyrimidine

A mixture of 27.2 g (0.2 mole) of 4-methoxy-benzaldehyde (Fluka 10440), 2.5 g of 3-methoxy-propionitrile, 70 ml of methanol and 3 g of potassium hydroxide is stirred at 60° C. for 8 hours, whereupon the reaction mixture is cooled, diluted with 500 ml of water and extracted twice with 100 ml of benzene each. The organic layer is dried and evaporated in vacuo. The residue is dissolved in 50 ml of diethylene glycol monomethyl ether, then 3 g of powdered sodium methylate are added, the mixture is heated to 75°–77° C. and stirred at this temperature for 3 hours. To the mixture 80 ml of isobutanol, 53 g of guanidine hydrochloride and a 30% methanolic solution of 27 g of sodium methylate are added. The reaction mixture is heated to 92° C. whereby methanol is distilled off. The reaction mixture is heated at this temperature for 7 hours, then cooled, the precipitated crystals are filtered and recrystallized from aqueous ethanol. Thus 23.2 g of the desired compound are obtained, yield 57%.

M.p.: 206°–209° C.

Analysis for the Formula $C_{12}H_{14}N_4O$: calculated: C%=62.59; H%=6.13; N%=24.33; found: C%=62.61; H%=5.96; N%=24.21.

EXAMPLES 2–7

In an analogous manner to Example 1 the following compounds are prepared:

EXAMPLE 2

2,4-Diamino-5-(3-methoxy-benzyl)-pyrimidine

The desired compound is prepared by using 3-methoxy-benzaldehyde (Fluka 64780) as starting material. M.p.: 221°–223° C.

Analysis for the Formula $C_{12}H_{14}N_4O$: calculated: C%=62.59; H%=6.13; N%=24.33; found: C%=62.58; H%=6.05; N%=24.21.

EXAMPLE 3

2,4-Diamino-5-(3,5-dimethoxy-benzyl)-pyrimidine

The desired compound is prepared by using 3,5-dimethoxy-benzaldehyde (Fluka 38630) as starting material. M.p.: 164°–168° C.

Analysis for the Formula $C_{13}H_{16}N_4O_2$: calculated: C%=59.98; H%=6.19; N%=21.56; found: C%=60.32; H%=6.26; N%=21.65.

EXAMPLE 4

2,4-Diamino-5-(2,4-dimethoxy-benzyl)-pyrimidine

The desired compound is prepared by using 2,4-dimethoxy-benzaldehyde (Fluka 38619) as starting material. m.p.: 170°–174° C.

Analysis for the Formula $C_{13}H_{16}N_4O_2$: calculated: C%=59.98; H%=6.19; N%=21.56; found: C%=60.02; H%=6.29; N%=21.35.

EXAMPLE 5

2,4-Diamino-5-(2,3-dimethoxy-benzyl)-pyrimidine

The desired compound is prepared by using 2,3-dimethoxy-benzaldehyde (Fluka 38610) as starting material. M.p.: 194°–198° C.

Analysis for the Formula $C_{13}H_{16}N_4O_2$: calculated: C%=59.98; H%=6.19; N%=21.56; found: C%=59.97; H%=6.27; N%=21.47.

EXAMPLE 6

2,4-Diamino-5-(3,4-methylenedioxy-benzyl)-pyrimidine

The desired compound is prepared by using 3,4-methylene-dioxy-benzaldehyde (Fluka 80820) as starting material.

M.p.: 248°–255° C.

Analysis for the Formula $C_{12}H_{12}N_4O_2$: calculated: C%=59.01; H%=4.95; N%=22.94; found: C%=59.45; H%=5.14; N%=22.66.

EXAMPLE 7

2,4-Diamino-5-(3-methoxy-4-ethoxy-benzyl)-pyrimidine

The desired compound is prepared by using 3-methoxy-4-ethoxy-benzaldehyde as starting material. M.p.: 195°–196° C.

Analysis for the Formula $C_{14}H_{18}N_4O_2$: calculated: C%=61.29; H%=6.61; N%=20.42; found: C%=60.84; H%=6.58; N%=20.00.

The 3-methoxy-4-ethoxy-benzaldehyde used as starting material can be prepared as follows:

To a solution of 30.4 g (0.2 mole) of vanilline, 12 g (0.3 mole) of sodium hydroxide and 300 ml of water, then 37.4 g (0.24 mole) of ethyl iodide are added. The reaction mixture is heated to boiling for 15 hours, then cooled and extracted with benzene. The extract is evaporated. The crude residue is dissolved in 110 ml of a 25% aqueous sodium hydroxide solution, clarified with activated charcoal and made alkaline to pH 12. The precipitated crystals are filtered, washed with water and dried. Thus 24.8 g of 3-methoxy-4-ethoxy-benzaldehyde are obtained, yield 69%, m.p.: 65°–67° C.

EXAMPLE 8

2,4-Diamino-5-(3-methoxy-4-allyloxy-benzyl)-pyrimidine-hydrochloride

One proceeds in an analogous manner to Example 1 except that 3-methoxy-4-allyloxy-benzaldehyde is used as starting material. The reaction mixture is worked up by dissolving the crude product in aqueous hydrochloric acid, clarifying the solution with activated charcoal, evaporating the solution, filtering the precipitated crystalline product, washing the same with aqueous alcohol and drying. The desired compound thus obtained melts at 236°–237° C.

Analysis for the Formula $C_{15}H_{18}N_4O_2 \cdot HCl$: calculated: C%=55.86; H%=5.93; N%=17.37;

Cl%=11.43; found: C%=55.73; H%=5.87; N%=17.21; Cl%=11.30.

The 3-methoxy-4-allyloxy-benzaldehyde used as starting material is prepared in an analogous manner to Example 7 except that allyl bromide is used. The refraction index of the light yellow oil thus obtained amounts to $n_D^{25}=1.5772$.

EXAMPLE 9

2,4-Diamino-5-(3-methoxy-4-n-butoxy-benzyl)-pyrimidine

The desired compound is prepared from 3-methoxy-4-n-butoxy-benzaldehyde in an analogous manner to Example 7.

M.p.: 143°–147° C.

Analysis for the Formula $C_{16}H_{22}N_4O_2$: calculated: C%=63.55; H%=7.33; N%=18.53; found: C%=63.12; H%=7.48; N%=18.40.

The 3-methoxy-4-n-butoxy-benzaldehyde used as starting material may be prepared in an analogous manner to Example 7 by using n-butyl bromide. The refraction index of the light yellow oil thus obtained amounts to $n_D^{25}=1.5535$.

EXAMPLE 10

2,4-Diamino-5-(3-methoxy-4-methoxyethoxy-benzyl)-pyrimidine

The desired compound is prepared from 3-methoxy-4-methoxyethoxy-benzaldehyde, m.p.: 163°–164° C.

Analysis for the Formula $C_{15}H_{20}N_4O_3$: calculated C%=59.19; H%=6.22; N%=18.41; found: C%=58.80; H%=6.59; N%=18.42.

The benzaldehyde starting material is prepared in an analogous manner to Example 7.

M.p.: 64°–67° C.

EXAMPLE 11

2,4-Diamino-5-(3-methoxy-4-benzyloxy-benzyl)-pyrimidine

The desired compound is prepared from 3-methoxy-4-benzyloxy-benzaldehyde.

M.p.: 198°–202° C.

Analysis for the Formula $C_{19}H_{20}N_4O_2$: calculated: C%=67.84; H%=5.99; N%=16.65; found: C%=67.40; H%=5.98; N%=16.35.

The 3-methoxy-4-benzyloxy-benzaldehyde used as starting material may be prepared in an analogous manner to Example 7, m.p.: 59°–63° C.

EXAMPLE 12

2,4-Diamino-5-(3-methoxy-4-hydroxy-benzyl)-pyrimidine-hydrobromide 10 g of 2,4-diamino-5-(3-ethoxy-4-benzyloxy-benzyl)-pyrimidine (Example 11) are dissolved in 500 ml of dioxane. Hydrogenation is carried out in the presence of 0.2 g of a palladium/charcoal catalyst under a pressure of 3 atm. and at 60°–65° C. When the calculated amount of hydrogen gas has been taken up, the catalyst is removed by filtration and the filtrate is evaporated in vacuo. The residue is dissolved in a mixture of 50 ml of water and 8 g of a 48% hydrogen bromide solution. After cooling the precipitated product is filtered and dried. Thus 7.9 g of the desired compound are obtained.

M.p.: 261°–263° C.

Analysis for the Formula $C_{12}H_{14}N_4O_2 \cdot HBr$: calculated: C%=44.05; H%=4.62; N%=17.12; Br%=24.44; found: C%=44.12; H%=4.63; N%=16.66; Br%=23.86.

II. Examples relating to the preparation of pharmaceutical compositions

EXAMPLE 13

Tablets having the following composition are prepared by methods of pharmaceutical industry known per se:

| Component | Amount, g/tablet |
|---|---|
| Compound of Example 1 | 0.200 |
| Lactose | 0.110 |
| Potato starch | 0.055 |
| Sodium amylopectin glycolate | 0.010 |
| Gelatine | 0.008 |
| Magnesium stearate | 0.001 |
| Total weight | 0.384 g |

EXAMPLE 14

Tablets having the following composition are prepared by methods of pharmaceutical industry known per se:

| Component | Amount, g/tablet |
|---|---|
| Compound of Example 2 | 0.400 |
| Lactose | 0.150 |
| Potato starch | 0.080 |
| Sodium amylopectin glycolate | 0.020 |
| Gelatine | 0.016 |
| Magnesium stearate | 0.002 |
| Total weight | 0.668 g |

EXAMPLE 15

Suppositories having the following composition are prepared by methods of pharmaceutical industry known per se:

| Component | Amount, g/suppository |
|---|---|
| Compound of Example 3 | 0.160 |
| Witepsol H 15 | 1.340 |

EXAMPLE 16

Suppositories having the following composition are prepared by methods of pharmaceutical industry known per se:

| Component | Amount, g/suppository |
|---|---|
| Compound of Example 4 | 0.250 |
| Witepsol H 15 | 1.500 |

EXAMPLE 17

Injectable solutions are prepared by methods of pharmaceutical industry known per se:

| Component | Amount |
|---|---|
| Compound of Example 8 | 0.1000 g |
| Ascorbic acid | 0.187 g |

-continued

| Component | Amount |
| --- | --- |
| Distilled water ad | 2.0 ml |

EXAMPLE 18

An injectable solution having the following composition is prepared by methods of pharmaceutical industry known per se:

| Component | Amount |
| --- | --- |
| Compound of Example 8 | 0.200 g |
| Ascorbic acid | 0.374 g |
| Distilled water ad | 5.0 ml |

EXAMPLE 19

A suspension having the following composition is prepared by methods of pharmaceutical industry known per se:

| Component | Amount |
| --- | --- |
| Compound of Example 10 | 2.0 g |
| Methyl-p-hydroxy-benzoate | 0.1 g |
| Spiritus anisatus | 0.25 g |
| Keltrol (xanthane gum) | 61.0 g |
| Distilled water ad | 100.0 ml |

What we claim is:

1. A method of treating an individual in need of an analgesic, anti-inflammatory agent, anti-anginal agent and/or antioxidant which comprises administering by oral, rectal or parental means, to an individual in need thereof, an effective amount of at least one 2,4-diamino-5-(substituted benzyl)pyrimidine of the formula

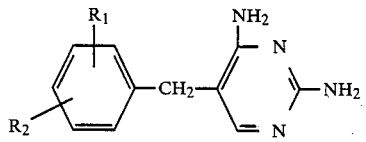

wherein
R$^1$ and R$^2$ may be the same or different and each stands for hydrogen, hydroxy, C$_{1-6}$ alkoxy, C$_{1-6}$ alkoxy-C$_{1-6}$ alkoxy, C$_{2-6}$ alkenyloxy or phenyl-(C$_{1-3}$ alkoxy), or R$^1$ and R$^2$ together form C$_{1-2}$ alkylenedioxy; with the proviso that at least one of R$^1$ and R$^2$ is other than hydrogen and with the further proviso that R$^1$ and R$^2$ cannot represent 3,4-dimethoxy substitution,
or a pharmaceutically acceptable acid addition salt thereof.

2. The method of claim 1, wherein said 2,4-diamino-5-(substituted benzyl)-pyrimidine is selected from the group consisting of
2,4-diamino-5-(4-methoxy-benzyl)-pyrimidine;
2,4-diamino-5-(3-methoxy-benzyl)-pyrimidine;
2,4-diamino-5-(3,5-dimethoxy-benzyl)-pyrimidine;
2,4-diamino-5-(2,4-dimethoxy-benzyl)-pyrimidine;
2,4-diamino-5-(2,3-dimethoxy-benzyl)-pyrimidine;
2,4-diamino-5-(3,4-methylenedioxy-benzyl)-pyrimidine;
2,4-diamino-5-(3-methoxy-4-ethoxy-benzyl)-pyrimidine;
2,4-diamino-5-(3-methoxy-4-allyloxy-benzyl)-pyrimidine;
2,4-diamino-5-(3-methoxy-4-n-butoxy-benzyl)-pyrimidine;
2,4-diamino-5-(3-methoxy-4-methoxyethoxy-benzyl)-pyrimidine;
2,4-diamino-5-(3-methoxy-4-benzyloxy-benzyl)-pyrimidine;
2,4-diamino-5-(3-methoxy-4-hydroxy-benzyl)-pyrimidine; mixtures thereof and pharmaceutically acceptable acid addition salts thereof.

3. The method of claim 1, wherein the hydrochloride salt of said 2,4-diamino-5-(substituted benzyl)-pyrimidine is administered to said patient.

4. The method of claim 1, wherein said 2,4-diamino-5-(substituted benzyl)-pyrimidine or pharmaceutically acceptable acid addition salt thereof is administered in the form of a tablet, capsule, pill, coated pill, dragee, solution, suspension, suppository or injection.

5. A pharmaceutical composition having an analgesic, antipyretic, anti-inflammatory, anti-anginal and/or antioxidant effect, comprising as active ingredient an effective amount of at least one 2,4-diamino-5-(substituted phenyl)-pyrimidine of the formula wherein
R$^1$ and R$^2$ may be the same or different and each stands for hydrogen, hydroxy, C$_{1-6}$ alkoxy, C$_{1-6}$ alkoxy-C$_{1-6}$ alkoxy, C$_{2-6}$ alkenyloxy or phenyl-(C$_{1-3}$ alkoxy), or R$^1$ and R$^2$ together form C$_{1-2}$ alkylenedioxy; with the proviso that at least one of R$^1$ and R$^2$ is other than hydrogen and with the further proviso that R$^1$ and R$^2$ cannot represent 3,4-dimethoxy substitution, or a pharmaceutically acceptable acid addition salt thereof in admixture with suitable inert solid or liquid carriers and/or auxilliary agents.

6. A pharmaceutical composition as defined in claim 5, wherein the active ingredient is
2,4-diamino-5-(4-methoxy-benzyl)-pyrimidine;
2,4-diamino-5-(3-methoxy-benzyl)-pyrimidine;
2,4-diamino-5-(3,5-dimethoxy-benzyl)-pyrimidine;
2,4-diamino-5-(2,4-dimethoxy-benzyl)-pyrimidine;
2,4-diamino-5-(2,3-dimethoxy-benzyl)-pyrimidine;
2,4-diamino-5-(3,4-methylenedioxy-benzyl)-pyrimidine;
2,4-diamino-5-(3-methoxy-4-ethoxy-benzyl)-pyrimidine;
2,4-diamino-5-(3-methoxy-4-allyloxy-benzyl)-pyrimidine;
2,4-diamino-5-(3-methoxy-4-n-butoxy-benzyl)-pyrimidine;
2,4-diamino-5-(3-methoxy-4-methoxyethoxy-benzyl)-pyrimidine;
2,4-diamino-5-(3-methoxy-4-benzyloxy-benzyl)-pyrimidine;
2,4-diamino-5-(3-methoxy-4-hydroxy-benzyl)-pyrimidine; or a mixture thereof or a pharmaceutically acceptable acid addition salt thereof.

7. A pharmaceutical composition as defined in claim 5 in a form suitable for oral, rectal or parenteral administration.

8. A pharmaceutical composition as defined in claim 7 in the form of a tablet, capsule, pill, coated pill, dragee, solution, suspension, suppository or injection.

9. A pharmaceutical composition as defined in claim 5, where said active ingredient is a hydrochloride of said 2,4-diamino-5-(substituted benzyl)-pyrimidine.

* * * * *